United States Patent [19]

Steinmetz et al.

[11] Patent Number: 4,806,676

[45] Date of Patent: Feb. 21, 1989

[54] CARBONYLATION PROCESS FOR PREPARATION OF AROMATIC CARBOXYLIC ESTERS AND AN ALKYL IODIDE

[75] Inventors: Guy R. Steinmetz; Mark Rule, both of Kingsport, Tenn.

[73] Assignee: Eastman Kodak Company, Rochester, N.Y.

[21] Appl. No.: 209,120

[22] Filed: Jun. 20, 1988

[51] Int. Cl.$^4$ .................. C07C 67/37; C07C 17/00
[52] U.S. Cl. ........................................ 560/80; 560/76; 560/97; 560/100; 560/102; 560/103; 570/181; 570/261
[58] Field of Search ............... 560/97, 100, 80, 102, 560/103; 570/181, 261

[56] References Cited

U.S. PATENT DOCUMENTS 2,565,462 10/1951 Prichard et al. .............. 560/97 X
3,988,358 10/1976 Heck .............................. 560/97 X

OTHER PUBLICATIONS

Nakayama and Mizoroki, Bulletin of the Chemical Society of Japan, vol. 42, pp. 1124–1129, (1969).

*Primary Examiner*—Werren B. Lone
*Assistant Examiner*—Vera C. Clarke
*Attorney, Agent, or Firm*—Charles R. Martin; W. P. Heath, Jr.

[57] ABSTRACT

A process for preparing an aromatic carboxylic ester and an alkyl iodide by carbonylating an aromatic iodide in the presence of an ether, a catalytic amount of a transition metal and a strong acid promoter.

13 Claims, No Drawings

CARBONYLATION PROCESS FOR PREPARATION OF AROMATIC CARBOXYLIC ESTERS AND AN ALKYL IODIDE

This invention relates to a novel carbonylation process for the preparation of both aromatic carboxylic esters and an iodine containing compound from which the iodine values can be economically recovered. The carbonylation is conducted in the presence of an ether and a transition metal catalyst with a strong acid promoter.

The carbonylation of aromatic halides in the presence of various Group VIII metal catalysts to obtain aromatic carboxylic acids and esters is well known in the art. For example, U.S. Pat. No. 3,988,358 discloses the palladium-catalyzed carbonylation of aromatic halides in the presence of an alcohol and a tertiary amine to produce the corresponding carboxylic acid ester. Nakayama and Mizoroki [Bull. Chem. Soc. Japan 42 (1969) 1124] disclose the nickel-catalyzed carbonylation of aromatic halides in the presence of an alcohol and potassium acetate to produce the corresponding acid ester.

While it is known that aromatic iodides can be carbonylated, the use of these materials has been discouraged by the cost associated with the difficulty of recovering the iodine values. For example, the use of basic materials in the carbonylation of aromatic halides, such as tri n-butyl amine in U.S. Pat. No. 3,988,358, results in the formation of halide salts from which the halide values can be reclaimed only through uneconomical procedures involving severe chemical treatments.

In U.S. Pat. No. 2,565,462, Prichard and Tabet disclose the carbonylation of aromatic halides to aromatic carboxylic esters in the presence of alcohols, ethers, and phenols using nickel tetracarbonyl. However, only non-catalytic quantities of iron; nickel, and cobalt are used as promoters under reaction conditions of both temperature and pressure that are much more severe than is shown by our invention.

U.S. Ser. Nos. 109,974, 115,292, 115,294, 115,295, and 166,948 disclose the carbonylation of aromatic iodides to aromatic carboxylic esters and alkyl iodides in the presence of an ether and a transition metal catalyst particular to each application. However, the carbonylation rates are slow in comparison to the present invention.

We have discovered a process which not only results in the carbonylation of aromatic iodides to aromatic carboxylic esters with low acid content in excellent yields and at excellent rates of conversion but also a process which results in production of alkyl iodides from which the iodine values can be economically recovered.

In this invention, the carbonylation is conducted in the presence of an ether and a catalytic amount of a transition metal catalyst with a strong acid promoter under aromatic carboxylic ester and alkyl iodide-forming conditions of temperature and pressure. The advantage afforded by our invention over the prior art is that the addition of the strong acid promoter results in a dramatic increase in the carbonylation rate of aromatic iodides when conducted in the presence of a transition metal catalyst and an ether.

The aromatic iodides which may be used in our process may be monoiodo or polyiodo, e.g., di-, tri- and tetra-iodo aromatic compounds. The aromatic nucleus or moiety can contain from 6 to 18 carbon atoms, preferably 6 to 10 carbon atoms an may be carbocyclic aromatic such as benzene, biphenyl, terphenyl, naphthalene, anthracene, etc., or heterocyclic aromatic such as pyridine, thiophene, pyrrole, indole, etc. In addition to one or more iodine atoms, the aromatic moiety may be substituted by various substituents substantially inert under the conditions employed in our process. Examples of such substituents include alkyl of up to about 12 carbon atoms such as methyl, ethyl, isobutyl, hexyl, 2-ethylhexyl, nonyl, decyl, dodecyl, etc.: cycloalkyl of about 5 to 12 carbon atoms such as cyclopentyl, cyclohexyl, 4-butylcyclohexyl, etc.; halogen such as chloro and bromo; alkoxycarbonyl of from 2 to about 8 carbon atoms such as methoxycarbonyl, ethoxycarbonyl, butoxycarbonyl, hexyloxycarbonyl, etc.; carboxyl; cyano; alkenyl of about 2 to 12 carbon atoms such as vinyl allyl, etc.; formyl; alkanoyl of about 2 to 8 carbon atoms such as acetyl, propionyl, butyryl, hexanoyl, etc.; alkanoylamido of about 2 to 8 carbon atoms such as acetamido butylamido, etc.; aroylamino such as benzamido; and alkylsulfonamide such as methanesulfonamide hexanesulfonamide, etc.

Specific examples of the aromatic iodide reactants include iodobenzene, 1,3- and 1,4-diiodobenzene 1,3,5-triiodobenzene, 4-iodotoluene, 4-iodophenyl, 4-iodoanisole, 4-iodoacetophenone, 4,4'-diiodobiphenyl, 4-chloroiodobenzene, 3-bromoiodobenzene and 2,6- and 2,7-diiodonaphthalene. Our process is particularly useful for the preparation of benzenedicarboxylic and naphthalenedicarboxylic esters with low acid content and thus the preferred reactants are diiodobenzenes, especially 1,3- and 1,4-diiodobenzene, and diiodonaphthalenes, especially 2,6- and 2,7-diiodonaphthalene.

The aromatic iodide reactants are known compounds and/or can be prepared according to published procedures. For example, T. Hudlicky et al., *The Chemistry of Halides, Pseudohalides and Azides*, Supplement D, Part 2, 1142–1158, the disclosure of which is incorporated herein by reference in its entirety discloses a number of such processes. Another process described in J. Chem. Soc. 150 (1952) comprises treating an aromatic compound, such as benzene, with iodine in the presence of silver sulfate dissolved in concentrated sulfuric acid.

The ether used in the process of this invention, which is preferably dimethyl ether, results in the formation of methyl carboxylate esters, which may be used in transesterification reactions, and produces methyl iodide which is the most volatile of the alkyl iodides. However, other ethers containing up to about 12 carbon atoms, preferably up to about 4 carbon atoms, may be employed if desired. Examples of other suitable ethers include diethyl ether, dipropyl ether, dibutyl ether, dipentyl ether, dihexyl ether, diheptyl ether, dioctyl ether, didecyl ether, dibenzyl ether, dioxane, anisole, or mixed dialkyl ethers. Mixture of these ethers may also be employed. For each mole equivalent of aromatic ester produced, one mole of ether is required.

The process provided by our invention can also be carried out in the presence of an organic solvent such as aliphatic, alicyclic and aromatic hydrocarbons, and halogenated hydrocarbons. Examples of such solvents include benzene, toluene, the xylenes, hexane, heptane, chlorobenzene, ethylene dichloride, methychloroform, naphthalene, etc. However, the use of a solvent is not critical to the practice of this invention. Water or potential esterifying agents such as alcohols and their carboxylate esters may also be present in the reaction mixture depending upon the desired ester to acid ratio.

The transition metal catalyst can be palladium, rhodium, nickel, ruthenium, or iridium, preferably palladium.

The palladium catalyst can be provided to the reaction medium as either palladium metal or as any of a number of palladium salts or complexes, such as palladium acetate. The amount of palladium is not significant as long as enough is present to catalyze the reaction. Preferably, the catalyst is present in a concentration of 1 to 0.0001 mole percent, preferably 0.025 to 0.001 mole percent, based on the moles of iodoaromatic reactant. Therefore, the total reaction medium has a catalyst concentration of about 1,000 ppm to 0.1 ppm with preferred catalyst concentrations of 250 to 1 ppm.

The rhodium catalyst can be provided to the reaction medium as either rhodium metal or as any of a number of rhodium salts or complexes. Illustrative sources of rhodium are rhodium trichloride, rhodium tribromide, rhodium triiodide, rhodium acetate, rhodium oxide, dicarbonyl rhodium acetylacetonate, rhodium carbonyl complexes and their phosphine and halogen substituted analogs. The amount of rhodium is not significant as long as enough is present to catalyze the reaction. Preferably, the catalyst is present in a concentration of 10 to 0.001 mole percent, preferably 1.0 to 0.1 mole percent, based on the moles of iodoaromatic reactant. Therefore, the total reaction medium has a catalyst concentration of about 10,000 ppm to 10 ppm with preferred catalyst concentrations 1,000 to 100 ppm.

The nickel catalyst can be provided to the reaction medium as either nickel metal or as any of a number of nickel salts or complexes, such as nickel iodide. The amount of nickel is not significant as long as enough is present ot catalyze the reaction. Preferably, the catalyst is present in a concentration of 10 to 0.001 mol percent, preferably 2.5 to 0.1 mole percent, based on the moles of iodaromtic reactant. Therefore, the total reaction medium has a catalyst concentration of about 10,000 to 1 ppm with preferred catalyst concentrations of 1,000 to 100 ppm.

The ruthenium catalyst can be provided to the reaction medium as any of a number of ruthenium salts or complexes that are capable of providing ruthenium in a soluble form in the reaction. Illustrative sources of ruthenium are ruthenium trichloride, ruthenium, tribromide, ruthenium triiodide, ruthenium acetate, ruthenium acetylacetonate, ruthenium dioxide, ruthenium tetraoxide, ruthenium pentacarbonyl and dodecacarbonyltriruthenium and their phosphine and halogen substituted analogs. The amount of ruthenium is not significant as long as enough is present to catalyze the reaction. Preferably, the catalyst is present in a concentration of 10 to 0.01 mole percent, preferably 1.0 to 0.1 mole percent, based on the moles of iodoaromatic reactant. Therefore, the total reaction medium has a catalyst concentration of about 10,000 to 10 ppm with preferred catalyst concentrations of 1,000 to 100 ppm.

The iridium catalyst can be provided to the reaction medium as any of a number of iridium salts or complexes that are capable of providing iridium in a solution form in the reaction. Illustrative sources of iridium are iridium trichloride, iridium tribromide, iridium triiodide, iridium acetylacetonate, iridium dioxide, and dodecacarbonyltetrairidium and their phosphine and halogen substituted analogs. The amount of iridium is not significant as long as enough is present in a concentration of 10 to 0.01 mole percent, preferably 1.0 to 0.1 mole percent based on the moles of aromatic iodide reactant. Therefore, the total reaction medium has a catalyst concentration of about 10,000 to 10 ppm with preferred catalyst concentrations of 1,000 to 100 ppm.

The strong acid promoter is added to the reaction medium to maintain and enhance the reaction rate of the carbonylation process. By the term "strong acid promoter" is meant any substance that can act as a proton donor or electron acceptor that results in the acceleration in the carbonylation of aromatic halides with ethers. Strong acids that do not contain strongly nucleophilic conjugate bases are preferable. The strong acid promoter can be added in an amount of about 0.01 to about 25 weight percent of the reaction medium. Examples of a strong acid promoters are tetrafluoroboric acid and methanesulfonic acid.

The carbonylation reaction is conducted in the presence of carbon monoxide, which is employed in amounts such that the total reaction pressure is suitable for the formation of both the aromatic carboxylic ester and the alkyl iodide. The carbon monoxide employed may be essentially pure or it may contain other gases such as carbon dioxide, hydrogen, methane and other compounds produced by synthesis gas plants. Normally, the carbon monoxide will be at least 90, preferably at least 95, percent pure.

The process of the present invention can be conducted at temperatures and pressures suitable for formation of both the aromatic carboxylic ester and alkyl iodide. The temperature and pressures are interdependent and can vary considerably. Normally, the pressure will be at least 100 psig. While the process can be carried out at pressures as high as 10,000 psig, the cost of utilities and equipment required for such high pressure operation may not be commercially justified. Thus, the pressure normally will be in the range of about 300 to 4,000 psig, preferably about 750 to 1,500 psig. A particularly preferred pressure is 1,000 psig. While temperatures as low as 125° C. and higher than 225° C. may be used, our process normally is carried out between about 150° to 275° C. The preferred temperature range is 180° to 250° C. A particularly preferred temperature is 220° C.

The relative amounts of carbon monoxide, ether and aromatic iodide used in our process can be varied substantially and are, in general, not critical. However, it is preferable to have at least stoichiometric amounts present relative to the aromatic iodide of complete conversion is desired.

When a polyiodo aromatic compound is used as the reactant in our carbonylation process, the products obtained include both aromatic polycarboxylic esters and partially carbonylated products such as iodoaromatic carboxylic esters. The latter compounds are useful as intermediates in the preparation of derivatives of aromatic carboxylic esters, for example, by displacement reactions whereby the iodo substituent is replaced with other radicals. The difunctional esters, such as dimethyl 2,6-naphthalenedicarboxylate, can be reacted with diols to produce high molecular weight polyesters suitable for molding plastics. Useful articles can be molded from these plastics, such as by injection molding. The relative amounts of partially or totally carbonylated products is highly dependent on the period of time that the reactant resides under carbonylation conditions.

The alkyl iodides prepared according to the process of our invention may be used in other chemical processes such as in the preparation of carboxylic acids and carboxylic anhydrides according to known carbonylation procedures. Alternatively, the alkyl iodide can be oxidatively decomposed at elevated temperatures to produce a gaseous mixture of iodine, carbon dioxide, and water from which the iodine can be recovered. Alternatively, the alkyl iodides may be thermally decomposed to iodine and an alkane, or hydrogenated to hydrogen iodide and methane.

Our process is carried out at a pKa of less than 5. Therfore, there are not significant amounts of basic materials which preferentially combine with hydrogen iodide and interfere with the formation of an alkyl iodide. Examples of such bases which are not present in significant amounts in our process include amines, particularly tertiary amines, and hydroxides, alkoxides and weak acid salts, e.g., carboxylates of the alkali and alkaline earth metals.

Our invention is further illustrated by the following examples. In the procedures utilized in the examples the materials employed except dimethyl ether are loaded into a 330-mL autoclave constructed of Hastelloy B2 alloy which is designed to operate in a rocking mode. The autoclave is pressurized with 200 psig carbon monoxide gas pressure at room temperature and then the gas is vented and the autoclave is sealed. In Examples 1–6, the autoclave is charged with the desired amount of dimethyl ether and then pressurized to a total pressure of 300 psig with carbon monoxide gas at ambient temperature and heated and rocked until reaction temperature was reached, at which time additional carbon monoxide gas is added to increase the autoclave internal pressure to the predetermined value. Reactor pressure is maintained by adding carbon monoxide at the same rate at which it is consumed by the reactants. The carbon monoxide used is esssentially pure. When the predetermined reaction time is completed, the autoclave is cooled by a stream of cold air to approximately 25° C. After the gas is vented from the autoclave the crude product is isolated by filtration and analyzed by gas chromatographic methods. The percent conversion is the mole percent of iodo-group converted to carboxylic acid or ester. The results are shown below.

| Example 1 | |
|---|---|
| Iodoaromatic | 2,6-diiodonaphthalene |
| Wt (g) | 30.0 |
| Catalyst | Palladium Acetate |
| Wt (g) | 0.01 |
| Ether | Dimethyl Ether |
| Vol (mL) | 42.0 |
| Solvent | 1-Methylnaphthalene |
| Wt (g) | 100.53 |
| Acid Promoter | — |
| Vol (mL) | — |
| Other | Water |
| Wt (g) | 0.52 |
| Time (Hour) | 1 |
| Pressure (psig) | 1,500 |
| Temp. (°C.) | 205 |
| % Conversion | 53 |

| Example 2 | |
|---|---|
| Iodoaromatic | 2,6-diiodonaphthalene |
| Wt (g) | 30.0 |
| Catalyst | Palladium Acetate |
| Wt (g) | 0.01 |
| Ether | Dimethyl Ether |
| Vol (mL) | 42.0 |
| Solvent | 1-Methylnaphthalene |
| Wt (g) | 100.31 |
| Acid Promoter | 49% Tetrafluoroboric Acid in Water |
| Vol (mL) | 1.00 |
| Other | — |
| Wt (g) | — |
| Time (Hour) | 1 |
| Pressure (psig) | 1,500 |
| Temp. (°C.) | 205 |
| % Conversion | 94 |

| Example 3 | |
|---|---|
| Iodoaromatic | 2,6-diiodonaphthalene |
| Wt (g) | 30.0 |
| Catalyst | Palladium Acetate |
| Wt (g) | 0.01 |
| Ether | Dimethyl Ether |
| Vol (mL) | 42.0 |
| Solvent | 1-Methylnaphthalene |
| Wt (g) | 100.32 |
| Acid Promoter | Tetrafluoroboric Acid-Diethyl Ether Complex |
| Vol (mL) | 1.00 |
| Time (Hour) | 1 |
| Pressure (psig) | 1,500 |
| Temp. (°C.) | 205 |
| % Conversion | 100 |

| Example 4 | |
|---|---|
| Iodoaromatic | 2,6-diiodonaphthalene |
| Wt (g) | 30.0 |
| Catalyst | Palladium Acetate |
| Wt (g) | 0.01 |
| Ether | Dimethyl Ether |
| Vol (mL) | 42.0 |
| Solvent | 1-Methylnaphthalene |
| Wt (g) | |
| Acid Promoter | Methanesulfonic Acid |
| Vol (mL) | 1.00 |
| Time (Hour) | 1 |
| Pressure (psig) | 1,500 |
| Temp. (°C.) | 205 |
| % Conversion | 62 |

| Example 5 | |
|---|---|
| Iodoaromatic | 2,6-diiodonaphthalene |
| Wt (g) | 30.0 |
| Catalyst | Palladium Acetate |
| Wt (g) | 0.01 |
| Ether | Dimethyl Ether |
| Vol (mL) | 42.0 |
| Solvent | 1-Methylnaphthalene |
| Wt (g) | 100.62 |
| Acid Promoter | Boron Trifluoride Etherate |
| Vol (mL) | 1.00 |
| Time (Hour) | 1 |
| Pressure (psig) | 1,500 |
| Temp. (°C.) | 205 |
| % Conversion | 44 |

| Example 6 | |
| --- | --- |
| Iodoaromatic | 2,6-diiodonaphthalene |
| Wt (g) | 30.0 |
| Catalyst | Palladium Acetate |
| Wt (g) | 0.01 |
| Ether | Dimethyl Ether |
| Vol (mL) | 42.0 |
| Solvent | 1-Methylnaphthalene |
| Wt (g) | |
| Acid Promoter | 48% Hydrofluoric Acid in Water |
| Vol (mL) | 1.00 |
| Time (Hour) | 1 |
| Pressure (psig) | 1,500 |
| Temp. (°C.) | 205 |
| % Conversion | 54 |

I claim:

1. A process comprising preparing an aromatic carboxylic ester and an alkyl iodide by carbonylating an aromatic iodide under aromatic carboxylic ester and an alkyl iodide-forming conditions of temperature and pressure in the presence of an ether, a catalytic amount of a transition metal selected from the group consisting of palladium, rhodium, nickel, ruthenium, and iridium and a strong acid promoter which does not contain strongly nucleophilic conjugate bases.

2. The process of claim 1 wherein the aromatic iodide is selected from the group consisting of diiodonaphthalene and diiodobenzene.

3. The process of claim 2 wherein the diiodonaphthalene is 2,6-diiodonaphthalene and the diiodobenzene is 1,4-diiodobenzene.

4. The process of claim 1 wherein the strong acid promoter is selected from the group consisting of tetrafluoroboric acid and methanesulfonic acid.

5. The process of claim 1 wherein the ether contains from 1 to 4 carbon atoms.

6. The process of claim 5 wherein the ether is dimethyl ether.

7. The process of claim 1 wherein the temperature is in the range of about 150° to 275° C.

8. The process of claim 7 wherein the temperature is in the range of about 180° to 250° C.

9. The process of claim 1 wherein the pressure is in the range of 125 to 4,000 psig.

10. The process of claim 9 wherein the pressure is in the range of 300 to 1,500 psig.

11. The process of claim 1 wherein the process is carried out in the presence of an organic solvent.

12. A process comprising preparing an aromatic dicarboxylic ester selected from the group consisting of dimethyl benzendicarboxylate and dimethyl naphthalenedicarboxylate and methyl iodide by carbonylating a diiodobenzene or a diiodonaphthalene in the presence of dimethyl ether an organic solvent, a catalytic amount of a palladium and tetrafluoroboric acid at a temperature of about 180° to 250° C. and a pressure of about 500 to 1,500 psig.

13. A process comprising preparing dimethyl 2,6-naphthalenedicarboxylate and methyl iodide by carbonylating 2,6-diiodonaphthalene in the presence of dimethyl ether, an organic solvent, a catalytic amound of palladium and tetrafluoroboric acid at a temperature of about 220° C. and a pressure of about 1,000 psig.

* * * * *